United States Patent [19]

Morgan, Jr.

[11] Patent Number: 4,900,841
[45] Date of Patent: Feb. 13, 1990

[54] 1-[4-[(METHYL-SULFONYL)AMINO]BENZOYL]AZIRIDINE

[75] Inventor: Thomas K. Morgan, Jr., Morris Plains, N.J.

[73] Assignee: Schering A.G., Berlin, Fed. Rep. of Germany

[21] Appl. No.: 39,875

[22] Filed: Apr. 20, 1987

[51] Int. Cl.$^4$ .......................................... C07D 203/02
[52] U.S. Cl. ...................................... 548/966; 564/99
[58] Field of Search ........................... 548/966; 564/99

[56] References Cited

U.S. PATENT DOCUMENTS

| 2,233,296 | 2/1941 | Nelles et al. | 564/99 |
| 4,242,273 | 12/1980 | Shepherd | 564/99 |
| 4,629,739 | 12/1986 | Davey et al. | 514/605 |

Primary Examiner—Mukund J. Shah
Assistant Examiner—Carol Lynn Cseh
Attorney, Agent, or Firm—Elizabeth A. Bellamy; John L. White; I. William Millen

[57] ABSTRACT

This invention relates to a process for the preparation of substituted sulfonamidobenzamides which compounds are known antiarrhythmic agents and to the novel N-acylaziridine employed therein.

1 Claim, No Drawings

1-[4-[(METHYL-SULFONYL)AMINO]BENZOYL-]AZIRIDINE

FIELD OF INVENTION

This invention relates to a process for the preparation of substituted sulfonamidobenzamides which compounds are known antiarrhythmic agents. More especially this invention relates to the preparation of N-[2-(substituted amino)ethyl]4-[(methylsulfonyl)amino]benzamides. This invention also relates to the novel compound 1-[4-[(methylsulfonyl)amino]benzoyl]aziridine and its use in the process of this invention.

GENERAL DESCRIPTION OF THE INVENTION

U.S. Pat. Nos. 4,544,654 issued Oct. 1, 1985 and 4,629,739 issued Dec. 16, 1986 both to D. Davey et al. describe novel substituted sulfonamidobenzamides and their use as antiarrhythmic agents more especially their use as class III antiarrhythmic agents.

This invention relates to the preparation of certain compounds described in the aforementioned patents of the following Formula I:

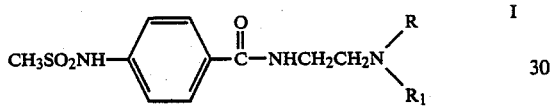

wherein R and $R_1$ are hydrogen, unsaturated lower alkyl, $C_1$-$C_{12}$ straight or branched chain alkyl, $C_3$-$C_6$ cycloaklyl, cycloalkyl(lower)alkyl, lower alkyl substituted by phenyl which may be substituted by up to three substituents selected from hydroxy or methoxy groups; with the provisos that:

(a) R and $R_1$ are not both hydrogen,
(b) the unsaturation cannot be alpha to the nitrogen atom.

In the foregoing Formula I lower alkyl shall refer to a straight or branched chain of from 1 to 4 carbon atoms, unsaturated lower alkyl shall refer to a straight or branched chain of from 3 to 4 carbon atoms having present a double or triple bond. Cycloalkyl shall be taken to mean a saturated carbocyclic of from 3 to 6 carbon atoms and cycloalkyl(lower)alkyl shall contain 4 to 10 carbon atoms.

The compounds of Formula I are of importance as Class III antiarrhythmic agents—for example such compounds as—(a)N-[2-(ethyl(heptyl)amino)ethyl]-4-[(methylsulfonyl)amino]benzamide, (b) N-[2-[[2-(3,4-dimethoxyphenyl)ethyl]amino]ethyl]-4-[(methylsulfonyl)amino]benzamide and (c) N-[2-(diethylamino)ethyl]-4-[(methylsulfonyl)amino]benzamide.

From the cited patents these compounds are most generally made by the following Method A, Method A

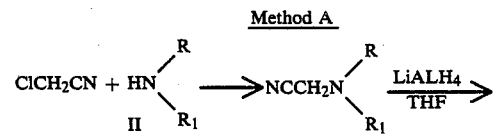

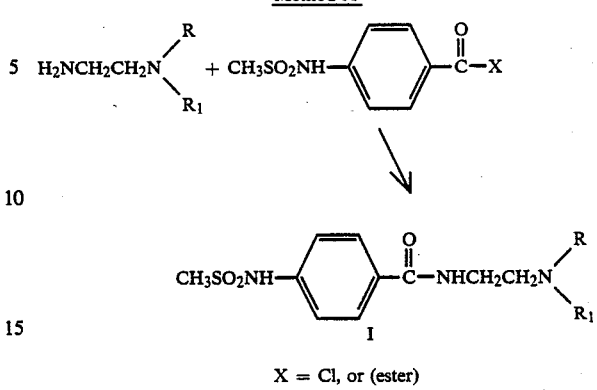

X = Cl, or (ester)

wherein R and $R_1$ are as previously described and X is chloro or methyl ester. For the previously enumerated compounds a,b & c, R and $R_1$ would be defined as follows—for:

Compound (a) R is $C_2H_5$, $R_1$ is $C_7H_{15}$
Compound (b) R is H,

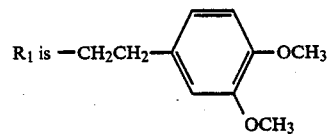

Compound (c) R is $C_2H_5$, and $R_1$ is $C_2H_5$.

The foregoing Method A involves the chloroacetonitrile alkylation of the primary or secondary amine (II) to incorporate the connecting chain onto the amino portion.

The following step is a lithium aluminum hydride reduction of the nitrile to provide the appropriately substituted ethylene diamine. This latter compound is then coupled with 4-[(methylsulfonyl)amino]benzoyl chloride or 4-[(methylsulfonyl)amino]benzoic acid methyl ester to produce the desired compound N-[2-(substituted amino)ethyl]-4-[(methylsulfonyl)amino]-benzamide.

The foregoing Method A whilst useful in the preparation of the compounds of Formula I (most especially where the appropriate ethylenediamine is commercially available) is not altogether desirable for the large scale production, nor in some instances for the initial production, of the compounds themselves. For instance, the reaction involves the use of chloroacetonitrile, a noxious substance, the following reaction includes a lithium aluminum hydride reduction to produce the ethylenediamine—a cumbersome reaction to be avoided if possible for safety reasons in a large scale environment (e.g., $H_2$ evolution on aqueous workup). Additionally, compounds of Formula I having a secondary amino function, e.g. where one of R or $R_1$ is hydrogen are difficult to prepare via Method A. The alkylation of the corresponding primary amine with chloroacetonitrile gives a mixture of some unreacted starting amine, desired secondary amine and some dialkylated tertiary amine. A further complication occurs with the coupling of the aroyl portion to the diamino compound wherein the two available nitrogens of the diamino moiety can yield a mixture of diaroyl compounds. These possible mixtures lead to lower yields and difficult separations.

The object then of this invention is to provide a safer and less complex method for the production of the N-[2-(substituted amino)ethyl]-4-[(methylsulfonyl)amino]benzamides of Formula I. Said object has been realized by the use of a novel intermediate and its reaction with a primary or secondary amine. The resultant Method B is as follows:

Method B

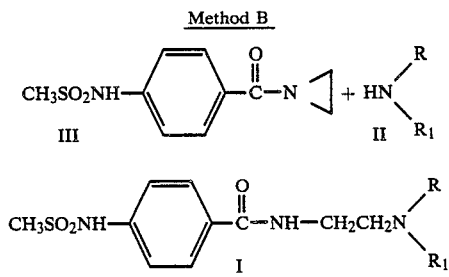

wherein R and $R_1$ are as previously defined. The novel N-acylaziridine intermediate disclosed in the above Method B is the compound 1-[4-[(methylsulfonyl)amino]benzoyl]aziridine (III) which compound is prepared by reacting 4-[(methylsulfonyl)amino]benzoyl chloride or the mixed anhydride of 4-[(methylsulfonyl)amino]benzoic acid and ethyl chloroformate with aziridine to produce the subject compound.

This novel N-acylaziridine is then subjected to nucleophilic ring opening by a primary or secondary amine II. This ring opening is accomplished by reacting the two reactants in a solvent medium such as a lower alkanol, lower alkylcyanide, DMF or DMSO at a temperature of from about 20° to about 120° C. in a time period sufficient to accomplish the complete nucleophilic ring opening of the N-acylaziridine. The end point of the reaction is determined by following the course of the reaction utilizing thin-layer chromatography.

The lower alkanol most generally used is methanol and the lower alkylcyanide most generally used is acetonitrile. Although the temperature of the reaction can be varied from 20° to 120° C.—most generally the reaction is conducted at a temperature around 50° C. The reaction has been found to generally take anywhere from 3 to 96 hours, most usually from 24 to 48 hours. In any case this nucleophilic ring opening of the N-acylaziridine can be followed to completion utilizing thin-layer chromatography.

Thus there is provided by this invention an alternate process as in Method B to produce the active antiarrhythmic agents of Formula I.

The invention described hereinbelow is illustrated below in the Examples, which, however are not to be construed as limiting the scope of this invention.

EXAMPLES

Example I

1-[4-[(Methylsulfonyl)amino]benzoyl]aziridine

A. 13.0 g (55.6 mmol) of 4-[(methylsulfonyl)amino]benzoyl chloride is suspended in 150 mL of methylene chloride and cooled to about 0° C. 2.40 g (55.7 mmol) of aziridine and 7.75 mL (55.6 mmol) of triethylamine are added and the reaction allowed to warm to room temperature and stir for 2 hours. After 2 hours, the solution is washed with 100 mL of saturated aqueous sodium chloride and placed in the freezer. After 18 hours, the resulting white precipitate is filtered, washed with 50 mL of ether and dried to provide the title compound.

NMR (CD$_3$CN): δ=2.41(s,4), 3.11(s,3), 7.09(br s,1), 7.27(d,2) and 8.08(d,2) ppm.

B. To a solution of 0.343 g (3.16 mmol) of ethyl chloroformate in 0.6 mL of acetone cooled to −10° C. under a nitrogen atmosphere add dropwise a solution of 1.0 g (3.16 mmol) of 4-[(methylsulfonyl)amino]benzoic acid triethylamine salt in 25 mL of acetone. Stir the mixture at −10° C. for 2 h then add slowly a solution of 0.136 g (3.16 mmol) of aziridine in 10 mL of acetone. Stir the reaction mixture for 30 min at ambient temperature after the addition is completed then remove the solvent in vacuo. Flash chromatograph the residue on silica gel with diethyl ether: methylene chloride (2:1), evaporate the solvent from the product containing fractions to obtain the title compound.

Example II

N-[2-(Ethyl(heptyl)amino)ethyl]-4-[(methylsulfonyl)amino]benzamide phosphoric acid salt 0.60 g (4.16 mmol) of N-ethylheptanamine and 0.50 g (2.08 mmol) of 1-[4-[(methylsulfonyl)amino]benzoyl]aziridine are dissolved in 10 mL of acetonitrile and the solution is warmed to 50° C. for 48 hours. The reaction is monitored by thin-layer chromatography (silica gel (EM); acetonitrile:conc. ammonium hydroxide (90:10)). After 48 hours, the reaction mixture is evaporated and the resultant solid is dissolved in 20 mL of methylene chloride. This solution is extracted with 2×10 mL of 1N aq. sodium hydroxide. The aqueous extract is acidified to pH=1 with 6N aq. hydrochloric acid and extracted with 2×15 mL of methylene chloride. The combined organic extracts are neutralized with saturated aqueous sodium bicarbonate and washed with 10 mL of water. The organic layer is dried over sodium sulfate, filtered and evaporated on a rotary evaporator to provide an oil. This oil is dissolved in 20 mL of 50% aqueous methanol and titrated to pH=4.5 with 0.1N aq. phosphoric acid. This solution is evaporated on the rotary evaporator and residual water is removed by azeotroping with 20 mL of alcohol. This residue is crystallized from 8 mL of reagent alcohol to provide the title compound.

NMR (DMSO-D$_6$): δ=0.74–0.92(t,3), 1.00–1.14(t,3), 1.14–1.34(m,8), 1.40–1.60(m,2), 2.60–2.96(m,6), 3.04(s,3), 3.36–3.56(m,2), 6.20–8.50(br s,4), 7.20–7.32(d,2), 7.80–8.00(d,2), and 8.80(br s,1) ppm.

Example III

N-[2-[[2-(3,4-Dimethoxyphenyl)ethyl]amino]ethyl][-(methylsulfonyl)amino]benzamide 4.5 g (18.73 mmol) of 1-[4-[(methylsulfonyl)amino]benzoyl]aziridine and 6.79 g of 2-(3,4-dimethoxyphenyl)ethylamine are dissolved in 100 mL of acetonitrile and heated at 50° C. for 48 hours. The reaction is monitored by thin-layer chromatography (silica gel (EM); acetonitrile). The solvent is concentrated to a 20 mL volume and the sample is purified by flash column chromatography using flash silica gel (Baker) and eluting with acetonitrile. The product fractions are combined and the solvent evaporated to provide residue which is dissolved in 50 mL of methanol, acidified with hydrochloric acid and placed in a freezer. The resulting precipitate is filtered to provide the title compound.

NMR (DMSO-d$_6$): δ=2.90(m,2), 3.05(s,3), 3.18(m,4), 3.63(quar,2), 3.73(s,3), 3.76 (s,3), 6.80(dd,1), 6.87(d,1), 6.88(d,1), 7.27(d,2), 7.91(d,2), 8.77(t,1), 8.95(br s,2) and 10.20(br s,1) ppm.

Example IV

N-[2-(Diethylamino)ethyl]-4-[(methylsulfonyl)amino]-benzamide hydrochloride 0.50 g (2.08 mmol) of 1-[4-[(methylsulfonyl)amino]-benzoyl]aziridine and 0.43 mL (4.16 mmol) of diethylamine are dissolved in 10 mL of acetonitrile and heated at 50° C. for 2 days. The reaction is monitored by thin-layer chromatography (silica gel (EM); acetonitrile:-conc. ammonium hydroxide (90:10)). After this time, the solvent is evaporated on the rotary evaporator. The crude residue is purified by flash column chromatography using flash silica gel (Baker) and eluting with acetonitrile/ammonium hydroxide gradient (0-5% ammonium hydroxide). The pure fractions are combined and the solvent evaporated and the residue is dissolved in 5 mL isopropanol, acidified with hydrochloric gas and cooled in a freezer overnight. The white precipitate is filtered to provide the title compound.

NMR (DMSO-$d_6$): $\delta$=1.24(t,6), 3.08(s,3), 3.20(m,6), 3.66(quar, 2), 7.30(d,2), 7.96(d,2), 8.96(m,1), 10.24(s,1), and 10.50 (s,1) ppm.

I claim:
1. A compound of the formula:

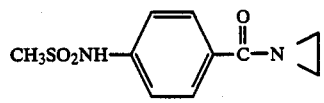

which is 1-[4-[(methylsulfonyl)amino]benzoyl]aziridine.

* * * * *